United States Patent [19]

Åström

[11] Patent Number: 5,055,409

[45] Date of Patent: Oct. 8, 1991

[54] METHOD FOR REDUCING INTERFERENCES IN THE ANALYSIS OF SUBSTANCES WHICH FORM VOLATILE HYDRIDES

[75] Inventor: Ove Åström, Holmsund, Sweden

[73] Assignee: BIFOK AB, Sollentuna, Sweden

[21] Appl. No.: 576,144

[22] Filed: Aug. 29, 1990

Related U.S. Application Data

[63] Continuation of Ser. No. 478,058, Feb. 7, 1990, abandoned, which is a continuation of Ser. No. 267,747, Nov. 2, 1988, abandoned, which is a continuation of Ser. No. 52,198, May 14, 1987, abandoned, which is a continuation of Ser. No. 376,006, May 7, 1982, abandoned.

[30] Foreign Application Priority Data

May 26, 1981 [SE] Sweden .............................. 8103321

[51] Int. Cl.$^5$ ........................................... G01N 35/08
[52] U.S. Cl. ...................................... 436/52; 436/73; 436/80; 436/84; 436/175; 436/182
[58] Field of Search .............. 436/52.53, 73, 149, 436/154, 171, 173, 77, 80, 84, 175, 182; 423/645

[56] References Cited

U.S. PATENT DOCUMENTS

| | | |
|---|---|---|
| 4,022,575 | 5/1977 | Hansen et al. . |
| 4,039,385 | 1/1982 | Harada et al. ............. 422/83 |
| 4,224,033 | 9/1980 | Hansen et al. ............. 422/81 |
| 4,230,665 | 10/1980 | Huber ......................... 436/73 |
| 4,314,824 | 2/1982 | Hansen et al. . |
| 4,391,776 | 7/1983 | Braun ......................... 436/73 |
| 4,399,225 | 8/1983 | Hansen et al. ............. 436/34 |

FOREIGN PATENT DOCUMENTS

| | | | |
|---|---|---|---|
| 466188 | 7/1975 | U.S.S.R. | .............. 423/645 |
| 874237 | 8/1961 | United Kingdom | .......... 423/645 |

OTHER PUBLICATIONS

Pierce et al., Applied Spectroscopy, vol. 30, No. 1, pp. 38–42, 1976.

Hawley, Condensed Chemical Dictionary, 8th Ed., van Nostrand, N.Y., 1971.

*Primary Examiner*—Robert J. Hill, Jr.
*Attorney, Agent, or Firm*—Poms, Smith, Lande & Rose

[57] ABSTRACT

Unsegmented, continuous flow analysis, FIA, has been modified for automated measurement of the amounts of metal and metalloids with volatile hydrides. The sample is injected into a continuous carrier flow of acid, and upon reaction with sodium borhydride in a mixing coil, a gaseous hydride is generated which is blown with a gas flow to a detector, preferably an electrically heated quartz tube, and the atomic absorption is measured. The chemical interferences from other substances have been eliminated to a substantial degree by kinetic discrimination. Samples of about 1–100 nanograms can be determined at a rate of 180 samples per hour and with a detection limit in the sub-ng range.

16 Claims, 1 Drawing Sheet

METHOD FOR REDUCING INTERFERENCES IN THE ANALYSIS OF SUBSTANCES WHICH FORM VOLATILE HYDRIDES

This application is a continuation of application Ser. No. 478,058, filed Feb. 7, 1990, now abandoned, which is a continuation of application Ser. No. 267,747, filed Nov. 2, 1988, now abandoned, which is a continuation of application Ser. No. 052,198, filed May 14, 1987, now abandoned, which is a continuation of application Ser. No. 376,006, filed May 7, 1982, now abandoned.

Hydride formation is usually used in combination with atomic adsorption spectroscopy for determining the amounts of substances forming covalent, volatile hydrides.

These substances from the C, N and O groups comprise 13 elements of which the following 8 have proved to form covalent hydrides in sufficient amounts for practical, analytical use, namely: As, Bi, Ge, Pb, Se, Sb, Sn and Te. Determination of the amounts of these substances is of importance for the control of water and discharges, for metallurgy, foodstuffs, various medicinal purposes, agriculture, mining, wine and tobacco, air etc.

The original technique with air-acetylene or argon-hydrogen flames has been replaced with heated absorption cells which give higher sensitivity. Many attempts have been made to increase sensitivity further and to eliminate the influence of interferences. Although the methods have been improved to a certain degree, many drawbacks still remain, such as poor control of the speed of reagent addition, low flexibility for the reagent mixing ratio, and limited control of the reaction time. Flow injection analysis (FIA) however, removes these disadvantages of the older methods, and the great flexibility of this technique allows it to be applied in the best manner to the particular substances to be analyzed.

The principles, apparatuses and procedures of FIA are presented in detail in U.S. Pat. Nos. 4,224,033 and 4,399,225 and U.S. Pat. Nos. 4,224,033 and 4,314,824.

BRIEF DESCRIPTION OF THE DRAWINGS

The invention will be described in more detail with reference to an embodiment and the accompanying drawings.

DETAILED DESCRIPTION OF THE PREFERRED EMBODIMENT

Within the scope of the invention, the analysis method can be varied in many different ways for different elements and to prevent interference by other substances.

In principle, the analysis proceeds as follows. The sample is dissolved in an acid to form a solution. The ion, metal or metalloid in question is then reduced by a powerful reducing agent to form a volatile hydride. Then, the volatile hydride is stripped from the solution using a gas, which is usually an inert gas, in a gas separator. This separated gas is led through a tube furnace to a spectrograph or some other suitable detector.

The FIA apparatus consists of a peristaltic pump 1 with several channels, a sample injector 2 with variable addition volume, flow meters, a gas-liquid separator 3, a detector and a recorder. With the exception of the pump hoses, hoses and tubes are made of polytetrafluoroethylene which is available from E. I. DuPont Co. as Teflon (registered trademark).

Figure 1:
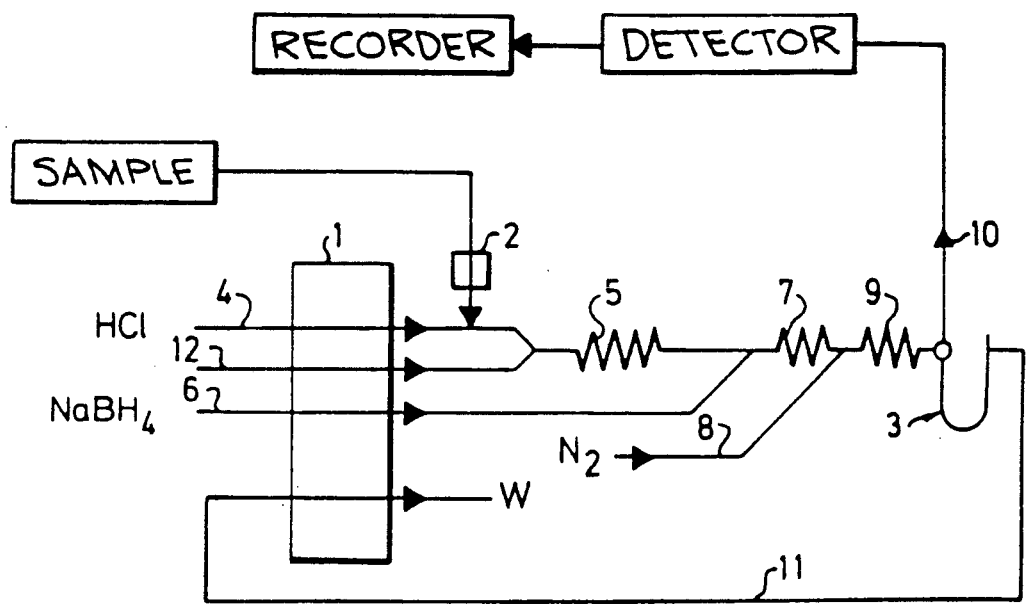
FIG. 1 shows the FIA apparatus according to the invention.

Acid, which in this case is HCl, is drawn through the hose 4 by the pump 1. The sample solution is added to the acid in hose 4 by the sample injector 2. The dispersion of the sample solution in the hydrochloric acid is effected in the coil 5, whereafter the reducing agent, in this case $NaBH_4$, is added by the pump 1 and the hose 6. Mixing takes place in the coil 7, whereafter gas, in this case nitrogen, for stripping the hydride is added through the hose 8 and is dispersed in the coil 9. The carrier stream in line 4 and coils 5, 7 and 9 entirely fills the tubing and coils during flow of liquid therethrough as is well-known in flow injection analysis. The gas is removed in the gas-liquid separator 3 and is conducted through line 10 to the quartz cell detector. The remaining solution is pumped off by the pump 1 through the hose 11 to a waste receptacle which is represented by W in FIG. 1. The point at which the sample is injected into line 4 may be viewed as a first location with the point at which gas is removed in the separator 3 being a second location. The sample flows as a discrete and controllably dispersed sample slug between the first and second locations as is well-known in flow injection analysis.

A further conduit 12 for adding additional acid or another reagent can be arranged to open into the hose 4 after the sample addition 2.

Analytically pure chemicals and freshly made solutions were used. Solutions with interfering ions were also made and their effect was tested. Such tested ions in solutions with a concentration of 100 ppm were K, Ca, Mg, Na, Cr, Cd, Co, Fe, Cu, Ni, Al, As, Sb, Sn, $CO_3$, $NH_4$, $PO_4$, $NO_3$ and $SO_4$.

The detector consisted of a quartz tube with an inner diameter of 6 mm and a length of 170 mm with a 1.3 mm quartz tube for the gas inlet fused to the middle of the tube. The quartz tube was wound with Kanthal wire, and the tube furnace was surrounded with an aluminum tube.

One of the greatest disadvantages of previous analysis apparatuses was the great amount of dead space in the equipment, generator, tubes, hoses and other components compared with the volume of the atomizer or furnace. In order to compensate for this, a large gas flow is used in order for the analytical signal to be reached within a reasonable time and in order for integration to provide a reasonably correct result. The FIA apparatus is designed to have a minimum of dead space, and all the coils are made of Teflon tubing with an inner diameter of 0.5 mm with the exception of the coil 5 which had an inner diameter of 0.7 mm. The gas-liquid separator has been made as small as possible, and in order to prevent excessive back pressure in the tube from the gas-liquid separator to the quartz cell, a short Teflon tube with an inner diameter of 1.5 mm is used. The overall dead volume of the system is only about half the atomizer volume.

It has been disclosed here how the actual analysis takes place with the aid of a tube furnace where the gas is heated and the amounts of the various substances are determined by spectrography. Other embodiments of the detector are also conceivable. For example, instead of nitrogen or another inert gas, it is possible to use hydrogen or a mixture of hydrogen and oxygen and to achieve the high temperature by direct combustion. The actual measurement can also be done by flame ionization or by electrochemical means. The analysis method is based on the basic principle of the FIA system that analysis is to be done quickly and simply.

Suitable detector systems include detection by atomic absorption spectroscopy, flame ionization spectroscopy, thermal conductometry, mass spectroscopy and electrochemical analysis. Atomic absorption spectroscopy in a heated quartz tube is also suitable.

Figure 2:
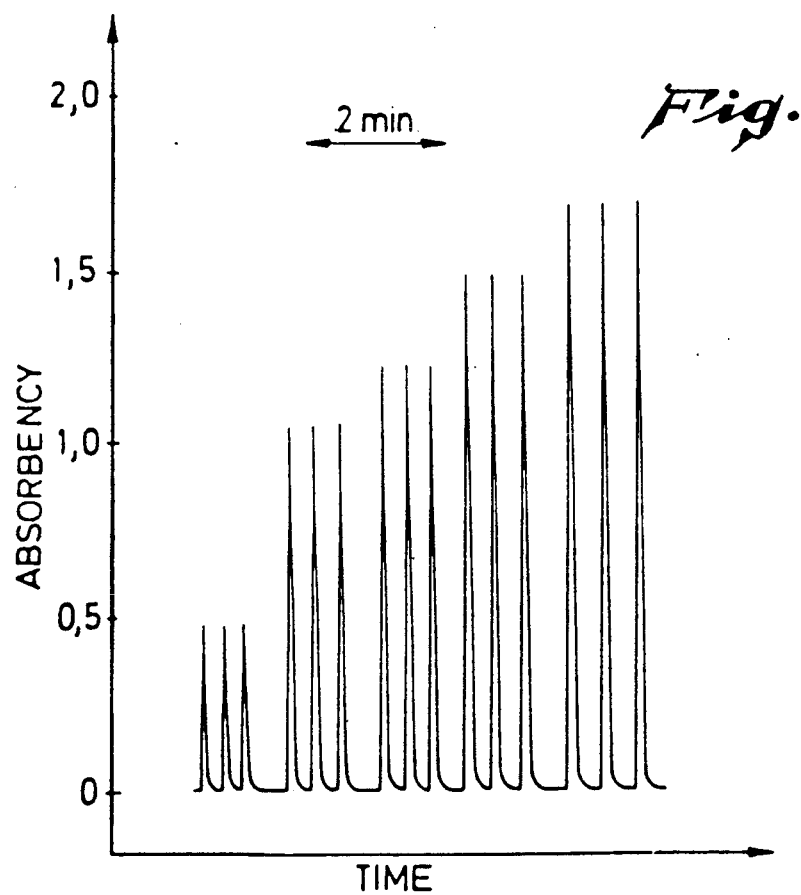
FIG. 2 shows an analysis curve for bismuth.

FIG. 2 shows the results of the analysis of bismuth, in which three different determinations were done for each sample. The values were taken from the peak heights since this proved to provide results which are more rapid and less sensitive to interference than integration of the curves. The length of coil 5 was 100 cm, coil 7 100 cm and coil 9 50 cm. The bismuth contents in the various samples were from left to right 10, 25, 30, 40 and 50 ppb.

The FIA system does not require any segmentation with air, for example, between the various samples. The required sample amount can vary between 300 $\mu$l and 1000 $\mu$l. It has been found that an increase of the sample amount from 300 to 700 $\mu$l increases the read-out by about 40%, while a further increase in the sample by 300 $\mu$l only produces an increase in the read-out by 10%. The final choice for sample volume was therefore 700 $\mu$l.

Various acids were tested and it was found that hydrochloric acid, nitric acid and sulphuric acid produce approximately equally good results. A concentration of 1.2M of hydrochloric acid is especially suitable for analyzing bismuth.

A number of ions can interfere with the results. Cobalt, nickel and copper have proved to be most troublesome. Sodium, potassium, calcium, magnesium, aluminum, $NO_3$, $PO_4$, $CO_3$, $NH_4$, iron, cadmium and chromium do not produce interference. The output signal increases with increasing flow speed, and at the same time the interferences are reduced. It has not, however, proved suitable to increase the flow rate to more than 8 ml per minute. By reducing the length of the reaction coils 7 and 9 and at the same time reducing the concentration of sodium borhydride, it is possible to reduce interference appreciably. By reducing the coil 5 to 10 cm and the sodium borhydride to 0.1%, interference by 100 ppm of cobalt in a sample solution was reduced appreciably. By completely removing the coil 5 and reducing the coil 9 further to 15 cm, a 25 ppb bismuth solution containing 875 ppm of cobalt could be measured without interference. It was shown that the effect of the sodium borhydride concentration on the height of the peak weakened appreciably with reduced coil length. Likewise, the stabilizing alkali amount in the borhydride solution can also be altered with good result.

The FIA system achieves controllable and reproducable dispersion of the sample in the carrier solution, and the apparatus can be optimized for various substances by selecting suitable coils.

The gas flow for stripping the hydride is of great importance, and the invention makes it possible with the FIA system to maintain a very low gas flow and thus achieve a higher hydride concentration in the gas to the detector.

What I claim is:

1. A method for reducing interferences which are produced during the detection of substances in a sample which are capable of forming volatile hydrides, wherein said sample includes interfering ions which interfere with the detection of said substances, said method comprising the steps of:

flowing a non-gas segmented liquid through a tube at a given flow speed to form a carrier stream which entirely fills said tube during continuous flow of said liquid therethrough;

injecting a sample into said continuous, non-gas segmented liquid carrier stream to form a discrete sample slug which is controllably dispersed therein;

adding acid to said carrier stream at a first location in an amount sufficient to treat said sample to form a discrete and controllably dispersed acid treated sample slug within said carrier stream;

adding a sufficient amount of a reducing agent to said acid treated sample slug to react with any of said substances in said sample to form volatile hydrides and a discrete and controllably dispersed reduced sample slug in said carrier stream from which any volatile hydrides formed are emitted;

flowing said discrete and controllably dispersed reduced sample slug in said carrier stream to a second location spaced a given distance from said first location, wherein said carrier stream continues to entirely fill said tube during flow from said first location to said second location;

increasing said flow speed of the carrier stream and detecting the amount of separated volatile hydrides and interfering ions at said second location as said flow speed is increased; and choosing a flow speed below 8 ml per minute wherein the amount of separated volatile hydrides is increased and the amount of interfering ions is simultaneously reduced.

2. The improved method according to claim 1 wherein said substances are selected from the group consisting of As, Bi, Ge, Pb, Se, Sb, Sn and Te.

3. The improved method according to claim 2 wherein said interfering ions are selected from the group consisting of cobalt, nickel and copper.

4. The improved method according to claim 3 wherein said reducing agent is sodium borohydride.

5. The improved method according to claim 2 wherein said reducing agent is sodium borohydride.

6. The improved method according to claim 1 wherein said interfering ions are selected from the group consisting of cobalt, nickel and copper.

7. The improved method according to claim 6 wherein said reducing agent is sodium borohydride.

8. The improved method according to claim 1 wherein said reducing agent is sodium borohydride.

9. A method for reducing interferences which are produced during the detection of substances in a sample which are capable of forming volatile hydrides, wherein said sample includes interfering ions which interfere with the detection of said substances, said method comprising the steps of:

flowing a non-gas segmented liquid through a tube at a given flow speed to form a carrier stream which entirely fills said tube during continuous flow of said liquid therethrough;

injecting a sample into said continuous, non-gas segmented liquid carrier stream to form a discrete sample slug which is controllably dispersed therein;

adding acid to said carrier stream at a first location in an amount sufficient to treat said sample to form a discrete and controllably dispersed acid treated sample slug within said carrier stream;

adding a sufficient amount of a reducing agent to said acid treated sample slug to react with any of said substances in said sample to form volatile hydrides and a discrete and controllably dispersed reduced sample slug in said carrier stream from which any volatile hydrides formed are emitted;

flowing said discrete and controllably dispersed reduced sample slug in said carrier stream to a second location spaced a given distance from said first location, wherein said carrier stream continues to entirely fill said tube during flow from said first location to said second location;

decreasing the amount of reducing agent and decreasing the distance between said first and second locations and detecting the amount of separated volatile hydrides and interfering ions at said second location as said reducing agent and distance are decreased; and choosing an amount of reducing agent and selecting a distance wherein the amount of interfering ions is reduced.

10. The improved method according to claim 9 wherein said substances are selected from the group consisting of As, Bi, Ge, Pb, Se, Sb, Sn and Te.

11. The improved method according to claim 10 wherein said interfering ions are selected from the group consisting of cobalt, nickel and copper.

12. The improved method according to claim 11 wherein said reducing agent is sodium borohydride.

13. The improved method according to claim 10 wherein said reducing agent is sodium borohydride.

14. The improved method according to claim 9 wherein said interfering ions are selected from the group consisting of cobalt, nickel and copper.

15. The improved method according to claim 14 wherein said reducing agent is sodium borohydride.

16. The improved method according to claim 9 wherein said reducing agent is sodium borohydride.

* * * * *